(12) United States Patent
Pöchlauer et al.

(10) Patent No.: US 6,781,012 B2
(45) Date of Patent: Aug. 24, 2004

(54) PROCESS FOR THE PREPARATION OF OPTICALLY AND CHEMICALLY HIGHLY PURE (R)- OR (S)-α-HYDROXYCARBOXYLIC ACIDS

(75) Inventors: Peter Pöchlauer, Linz (AT); Herbert Mayrhofer, Engerwitzdorf (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 0 days.

(21) Appl. No.: 09/834,926

(22) Filed: Apr. 16, 2001

(65) Prior Publication Data

US 2001/0041359 A1 Nov. 15, 2001

(30) Foreign Application Priority Data

Apr. 17, 2000 (AT) .......................................... A 670/2000

(51) Int. Cl.$^7$ .......................... C07C 57/00; C07C 59/48
(52) U.S. Cl. ...................................... 562/401; 562/470
(58) Field of Search .................................. 562/401, 470

(56) References Cited

U.S. PATENT DOCUMENTS

| | | | | |
|---|---|---|---|---|
| 4,105,783 | A | * | 8/1978 | Yu et al. |
| 4,859,784 | A | * | 8/1989 | Effenberger et al. |
| 4,983,771 | A | * | 1/1991 | Bryker et al. |
| 5,580,765 | A | * | 12/1996 | Hashimoto et al. |

OTHER PUBLICATIONS

Collet et al , Bulletin de la Société Chimique de France 1973, 12, Pt. 2, pp. 3330–3334,with English translation, pp. 1–18.*

Collet et al, "No. 630. –Etude Des Melange D'antipode Optiques. V.–Acides Mandeliques Substitues." Bulletin de la Société Chimique de France 1973, 12, Pt. 2, pp. 3330–3334.*

McMasters, Chem2O06 Laboratory Manual 1997, Expt. 1, Part B. Recrystallization and Melting Point Determinations. from world wide web :chemistry.mcmaster.ca/–chem2o6/labmanual/microscale/ms–recrs.html).*

* cited by examiner

Primary Examiner—Johann Richter
Assistant Examiner—Paul A. Zucker
(74) Attorney, Agent, or Firm—Wenderoth, Lind & Ponack, L.L.P.

(57) ABSTRACT

Process for the preparation of optically highly pure (R)- and (S)-α-hydroxycarboxylic acids, in which either isolated, impure (R)- and (S)-α-hydroxycarboxylic acids prepared by acidic hydrolysis of the (R)- and (S)- cyanohydrins obtained by enzyme-catalyzed addition of a cyanide group donor to the corresponding aldehydes or ketones are recrystallized in an aromatic hydrocarbon, optionally in the presence of a cosolvent, and optically highly pure (R)- and (S)-α-hydroxycarboxylic acids having an optical purity of over 98%ee are obtained or the hydrolysis solution obtained by acidic hydrolysis of the (R)- and (S)-cyanohydrins is treated directly with an aromatic hydrocarbon, optionally in combination with a cosolvent, and is then extracted at hydrolysis temperature, whereupon after cooling of the organic phase the corresponding chemically and optically highly pure (R)- and (S)-α-hydroxycarboxylic acids having an optical purity of over 98%ee crystallize out.

6 Claims, No Drawings

PROCESS FOR THE PREPARATION OF OPTICALLY AND CHEMICALLY HIGHLY PURE (R)- OR (S)-α-HYDROXYCARBOXYLIC ACIDS

Optically active α-hydroxycarboxylic acids are used, for example, as additives to foodstuffs or for the obtainment of pharmaceutical active compounds, vitamins and liquid-crystal use.

These optically active α-hydroxycarboxylic acids can further be advantageously converted, for example according to Effenberger et al., Angew. Chem. 95 (1983) No. 1, page 50, into N-substituted optically active α-amino acids which can otherwise only be prepared with very great difficulty.

Chiral α-hydroxycarboxylic acids are nowadays accessible chemically, fermentatively or enzymatically. The acid-catalyzed hydrolysis of cyanohydrins is an important preparation variant here. Thus racemic cyanohydrins, for example, can be hydrolyzed with addition of suitable microorganisms to the desired chiral α-hydroxycarboxylic acids. It is also known, for example from Angew. Chem. 1994, 106, page 1615f., that optically active cyanohydrins which, for example, are readily obtainable by means of enzyme-catalyzed synthesis can be hydrolyzed without racemization to the corresponding chiral α-hydroxycarboxylic acids. The optical purity of the chiral α-hydroxycarboxylic acid prepared in this way in this case corresponds to the optical purity of the chiral cyanohydrin employed, even if this is obtained in situ by enzyme-catalyzed addition of a cyanide group donor to an appropriate aldehyde or a ketone and additionally processed without isolation or purification. The working-up of α-hydroxycarboxylic acids prepared in this way was previously carried out by means of extraction. This optical purity, however, may be too low for certain fields of application of the α-hydroxycarboxylic acids, for example in the case of application in the pharmaceutical field, so that there was the necessity or it was an object of the invention to find a possibility of simultaneously increasing the chemical and the optical purity of the α-hydroxycarboxylic acids in a simple way, without a great loss of yield. Unexpectedly, it was possible to achieve this object by a crystallization step in an aromatic hydrocarbon.

The invention accordingly relates to a process for the preparation of chemically and optically highly pure (R)- and (S)-α-hydroxycarboxylic acids, which comprises recrystallizing impure (R)- and (S)-α-hydroxycarboxylic acids, prepared by acidic hydrolysis of the (R)- and (S)-cyanohydrins obtained by enzyme-catalyzed addition of a cyanide group donor to the corresponding aldehydes or ketones, in an aromatic hydrocarbon, optionally in the presence of a cosolvent, and obtaining chemically and optically highly pure (R)- and (S)-α-hydroxycarboxylic acids having an optical purity of over 98%ee.

In the process according to the invention, impure (R)- and (S)-α-hydroxycarboxylic acids are converted into highly pure (R)- and (S)-α-hydroxycarboxylic acids having an optical purity of over 98%ee.

The starting compounds used are (R)- and (S)-α-hydroxycarboxylic acids which are obtained by acidic hydrolysis of the corresponding (R)- and (S)-cyanohydrins, which in turn are prepared by enzymatic addition of a cyanide group donor to the corresponding aldehydes or ketones.

The enzymatic addition of a cyanide group donor to the corresponding aldehydes or ketones can be carried out here analogously to the prior art, for example analogously to EP 0 951 561, EP 0 927 766, EP 0 632 130, EP 0 547 655, EP 0 326 063 etc.

Suitable starting compounds are the aldehydes and ketones cited in the prior art.

Examples of suitable aldehydes here are aliphatic, aromatic or heteroaromatic aldehydes. Aliphatic aldehydes are understood here as meaning saturated or unsaturated aliphatic, straight-chain, branched or cyclic aldehydes. Preferred aliphatic aldehydes are straight-chain aldehydes in particular having 2 to 18 C atoms, preferably from 2 to 12, which are saturated or mono- or polyunsaturated. The aldehyde here can have both C—C double bonds and C—C triple bonds. The aldehyde can be unsubstituted or mono- or polysubstituted by groups which are inert under the reaction conditions, for example by optionally substituted aryl or heteroaryl groups, such as phenyl or indolyl groups, cycloalkyl groups optionally substituted by $C_1$–$C_6$–alkyl, which can contain one or more heteroatoms from the group consisting of O, S, P and N, or halogen, ether, alcohol, acyl, carboxylic acid, carboxylic acid ester, nitro or azido groups.

Examples of aromatic or heteroaromatic aldehydes are benzaldehyde and variously substituted benzaldehydes such as 2-chlorobenzaldehyde, 3,-4-difluorobenzaldehyde, 3-phenoxybenzaldehyde, 4-fluoro-3-phenoxybenzaldehyde, furthermore furfural, anthracene-9-carbaldehyde, furan-3-carbaldehyde, indole-3-carbaldehyde, naphthalene-1-carbaldehyde, phthalaldehyde, pyrazole-3-carbaldehyde, pyrrole-2-carbaldehyde, thiophene-2-carbaldehyde, isophthalaldehyde or pyridine aldehydes etc.

Examples of ketones are aliphatic, aromatic or heteroaromatic ketones in which the carbonyl carbon atom is unidentically substituted. Aliphatic ketones are understood as meaning saturated or unsaturated, straight-chain, branched or cyclic ketones. The ketones can be saturated or mono- or polyunsaturated. They can be unsubstituted, or mono- or polysubstituted by groups which are inert under the reaction conditions, for example by optionally substituted aryl or heteroaryl groups such as phenyl or indolyl groups, or by halogen, ether, alcohol, acyl, carboxylic acid, carboxylic acid ester, nitro or azido groups.

Examples of aromatic or heteroaromatic ketones are acetophenone, indolylacetone etc.

The corresponding (R)- or (S)- cyanohydrin is then hydrolyzed using concentrated hydrochloric acid, for example after extraction or after filtering off the enzyme and distilling off the solvent, without further purification analogously to the prior art, for example as described in Angew. Chem. 1994, 106, p. 1615 or in Tetrahedron Letters, Vol. 31, No. 9, pp. 1249–1252, 1990.

The crude (R)- and (S)-α-hydroxycarboxylic acids thus obtained, which have approximately the same optical purity as the corresponding (R)- and (S)-cyanohydrins, are then isolated from the reaction mixture by extraction and recrystallized according to the invention in an aromatic hydrocarbon, optionally in the presence of a cosolvent.

Suitable aromatic hydrocarbons here are toluene, xylenes, benzene or substituted benzenes, such as ethylbenzene, isopropylbenzene or chlorobenzenes. Toluene and xylene are preferably employed.

Suitable cosolvents are those solvents which increase the solubility of the hydroxycarboxylic acid in the organic phase and which are readily separable by distillation. Examples of these are optionally cyclic ethers, such as tetrahydrofuran, methyl tert-butyl ether, dimethoxyethane etc. or ketones such as methyl isobutyl ketone etc.

The amount of cosolvent here is approximately 5 to 50% by volume, preferably 10 to 30% by volume, based on the total amount of solvent.

The α-hydroxycarboxylic acid to be purified is dissolved in the appropriate solvent or solvent mixture with warming, whereupon, after separation of the phases, some of the solvent or of the solvent mixture is distilled off from the organic phase to remove the water and the mixture is then slowly cooled to 15–50° C. After a standing time of a few minutes up to a number of hours (5 minutes to 20 hours, longer standing times are also possible if necessary), the crystallized product is filtered off, and the crystallizate is preferably washed 1 to 5 times with the same solvent and dried. (R)- and (S)-α-hydroxycarboxylic acids having an optical purity of over 98%ee are obtained here. The process according to the invention in this case makes it possible to separate off over 90% of the impurities in one working step.

Preferably, the process according to the invention is employed for aromatic (R)- and (S)-α-hydroxycarboxylic acids of the formula Ar—$(CH_2)_n$CH(OH)$CO_2$H. In the formula Ar—$(CH_2)_n$CH—R—$CO_2$H, n is 0, or an integer from 1 to 5 and Ar is an unsubstituted or mono- or polysubstituted aryl or heteroaryl radical, such as phenyl, benzyl, naphthyl, pyridyl, furyl etc., suitable substituents being, for example, OH, $C_1$–$C_4$-alkyl or -alkoxy, thioalkyl, halogen, optionally substituted phenyl or phenoxy, amino or nitro.

Particularly preferably, n=0, 1 or 2 and Ar is an aryl radical, in particular phenyl, which can be unsubstituted or preferably substituted by $C_1$–$C_4$-alkyl or -alkoxy, OH, Cl, Br, phenyl, phenoxy or fluorophenoxy.

In a very preferred embodiment, the process according to the invention is used for the purification of (R)-2-chloromandelic acid.

In this case, optically active (R)-2-chloromandelonitrile is first prepared by. enzyme-catalyzed addition of hydrocyanic acid to 2-chlorobenzaldehyde by means of R-oxynitrilase, the cyanohydrin is isolated from the reaction mixture by extraction and solvent is distilled off. The cyanohydrin in this case has an enantiomeric excess of approximately 89–92%ee (about 95% R and about 5% S).

Without further purification, the cyanohydrin is hydrolyzed in concentrated hydrochloric acid under customary conditions, such as 60° C. and a time of 24 hours, and the corresponding hydroxycarboxylic acid is then extracted. As known from the prior art, no racemization occurs in the hydrolysis, so that the crude product likewise has an optical purity of approximately 89–92%ee (about 95% R and about 5% S). Owing to the crystallization according to the invention in an aromatic hydrocarbon, optionally in the presence of a cosolvent; in addition to the chemical purity the optical purity is also improved in an extremely simple and economical manner and optically highly pure (R)-2-chloromandelic acid having an optical purity of over 98%ee with over 99% of R form and less than 1% of S form is obtained.

Further, it is possible to couple the crystallization step according to the invention directly to the hydrolysis step, so that the hitherto customary extraction of the α-hydroxycarboxylic acids from the reaction mixture with ethers used in the prior art as extracting agents, such as methyl tert-butyl ether or diethyl ether, is unnecessary.

According to the invention, an aromatic hydrocarbon, optionally in combination with a cosolvent, is added here to the hydrolysis solution obtained after the hydrolysis, carried out according to the prior art, of the corresponding cyanohydrin in aqueous acidic solution at hydrolysis temperature (30 to 110° C.).

Suitable aromatic hydrocarbons here are, in turn, toluene, xylenes, benzene, or substituted benzenes, such as ethylbenzene, isopropylbenzene or chlorobenzenes. Toluene and xylene are preferably employed. Suitable cosolvents are, in turn, the solvents already mentioned.

After extracting 1 to 5 times, preferably 1 to 3 times, with the appropriate aromatic hydrocarbon or solvent mixture, the aqueous phases are discarded, whereupon some of the solvent or of the solvent mixture is preferably distilled off from the combined organic phases to remove the water and the residual organic phase is then cooled, whereby a chemically and optically highly pure α-hydroxycarboxylic acid crystallizes out which has an optical purity of over 98%ee. The crystallizate is then filtered off, optionally washed and freed from solvent residues, and dried.

The crystallization according to the invention coupled directly to the hydrolysis step, owing to which an additional isolation step is unnecessary, is likewise suitable for all (R)- and (S)- cyanohydrins which are prepared by enzymatic addition of a cyanide group donor to the corresponding aldehydes or ketones.

A further subject of the present invention is accordingly a process for the preparation of chemically and optically highly pure (R)- and (s)-α-hydroxycarboxylic acids, which comprises treating the hydrolysis solution obtained by acidic hydrolysis of the (R)- and (S)-cyanohydrins, prepared by enzyme-catalyzed addition of a cyanide group donor to the corresponding aldehydes or ketones, directly with an aromatic hydrocarbon, optionally in combination with a cosolvent, then extracting the mixture at hydrolysis temperature, whereupon after cooling of the organic phase the corresponding chemically and optically highly pure (R)- and (S)-α-hydroxycarboxylic acids crystallize out with an optical purity of over 98%ee.

Preferably, the process according to the invention is in turn employed for aromatic (R)- and (S)-α-hydroxycarboxylic, acids of the formula Ar—$(CH_2)_n$CH(OH)$CO_2$H. In the formula Ar—$(CH_2)_n$CH—R—$CO_2$H, n is 0, or an integer from 1 to 5 and Ar is an unsubstituted or mono- or polysubstituted aryl or heteroaryl radical, such as phenyl, benzyl, naphthyl, pyridyl, furyl etc., suitable substituents being, for example, OH, $C_1$–$C_4$-alkyl or -alkoxy, thioalkyl, halogen, optionally substituted phenyl or phenoxy, amino or nitro.

Particularly preferably, n=0, 1 or 2 and Ar is an aryl radical, in particular phenyl, which can be unsubstituted or preferably substituted by $C_1$–$C_4$-alkyl or -alkoxy, OH, Cl, Br, phenyl, phenoxy or fluorophenoxy.

In a very preferred embodiment, the process according to the invention is used for the preparation of chemically and optically highly pure (R)-2-chloromandelic acid.

In this case, optically active (R)-2-chloromandelonitrile is first prepared by enzyme-catalyzed addition of hydrocyanic acid to 2-chlorobenzaldehyde by means of R-oxynitrilase, the cyanohydrin is isolated from the reaction mixture by extraction and solvent is distilled off. The cyanohydrin in this case has an enantiomeric excess of approximately 89–92%ee (about 95% R and about 5% S).

Without further purification, the cyanohydrin is hydrolyzed in concentrated hydrochloric acid under customary conditions, such as 60° C. and a time of 24 hours, and the hydrolysis solution thus obtained is then treated directly with an aromatic hydrocarbon, instead of the hitherto customary ether, optionally in combination with a cosolvent, and the mixture is extracted 1 to 5 times. The aqueous phases are discarded; the chemically and optically highly pure (R)-2-chloromandelic acid crystallizes out from the combined organic phases by cooling thereof. Owing to the coupling according to the invention of the crystallization to the hydrolysis, in addition to the chemical purity the optical purity is also improved in an extremely simple and economical manner and chemically and optically highly pure (R)-2-chloromandelic acid having an optical purity of over 98%ee with over 99% of R form and less than 1% of S form is obtained.

A further subject of the present invention are accordingly optically and chemically highly pure (R)- and (S)-α-hydroxycarboxylic acids having an optical purity of over 98%ee, which are prepared by one of the processes according to the invention.

EXAMPLE 1

453.5 g of R-2-chloromandelonitrile were stirred at 63° C. for 24 hours in 925 ml of conc. hydrochloric acid. After cooling, the mixture was treated with 812 ml of water and 1255 ml of tert-butyl methyl ether and vigorously stirred. The phases were separated and the aqueous phase was then again extracted with 1255 ml of tert-butyl methyl ether. The combined organic phases were then extracted with 185 ml of water. The solvent was distilled off in vacuo from the dark-brown organic phase.

The final weight was 497.3 g and the enantiomeric purity of the brown crude product was determined by means of GC analysis (91.5%ee=95.7% R and 4.3% S).

The crude product was dissolved in 2780 ml of xylene by heating to 100° C. The solution was then slowly cooled to 21° C., crystallization commencing at 88° C. After a standing time of 16 hours, the crystallizate was filtered off and washed on the filter with 200 ml of xylene.

The product was then additionally washed once with 880 ml of xylene and twice with 550 ml of xylene. After sucking dry, the solvent residues were removed at 60° C. and 10 mbar.

405.9 g of white, crystalline R-2-chloromandelic acid of 98.1%ee (99.05% R and 0.95% S enantiomer) were obtained.

The mother liquor was concentrated in a rotary evaporator, a dark-brown viscous mass remaining as a residue. The 2-chloromandelic acid contained therein had an enantiomeric ratio of 51.9% R to 48.1% S.

EXAMPLE 2

16.2 g of R-2-chloromandelonitrile were stirred at 63° C. for 24 hours in 32 ml of conc. hydrochloric acid. The mixture was heated to 76° C. and treated with 100 ml of xylene and vigorously stirred. The phases were separated and the aqueous phase was then again extracted with 50 ml of xylene.

Some of the solvent was distilled off in vacuo to remove water from the dark-brown organic phase which contained R-2-chloromandelic acid of 91.4%ee. The mixture was then slowly cooled to 21° C., where crystallization commenced. After a standing time of 16 hours, the crystallizate was filtered off and washed on the filter with 8 ml of xylene.

The product was then additionally washed once with 31 ml of xylene and twice with 20 ml of xylene. After sucking dry, the solvent residues were removed at 60° C. and 10 mbar.

Highly pure R-2-chloromandelic acid of 99.2%ee was obtained.

EXAMPLE 3

42.3 ml of a solution of 16.2 g of R-2-chloromandelonitrile in 32 ml of conc. hydrochloric acid obtained by hydrolysis was divided into 5 ml portions, extracted at 80° C. with 15 ml of solvents or solvent mixtures indicated in the table and the contents of R-2-chloromandelic acid indicated, having an enantiomeric purity of 91.4% ee, were obtained in the org. phase.

| Extracting agent | Mixing ratio | Content of product in the organic phase |
| --- | --- | --- |
| xylene/tetrahydrofuran | 80/20 | 1.79 g |
| xylene/methyl isobutyl ketone | 80/20 | 1.60 g |
| xylene/dimethoxyethane | 80/20 | 1.42 g |
| xylene | — | 0.63 g |
| toluene | — | 0.79 g |

Water was then distilled off with some of the organic phase and by cooling the organic phase highly pure R-2-chloromandelic acid having an enantiomeric purity of over 98%ee was obtained. In some cases, enantiomeric purities of over 99%ee were obtained; thus the use of xylene resulted in an enantiomeric purity of 99.2%ee and the use of xylene/tetrahydrofuran in an enantiomeric purity of 99.9%ee.

EXAMPLE 4

13.1 g of R-2-chloromandelonitrile (enantiomeric purity: 91.2%ee) were stirred at 63° C. for 24 hours in 30 ml of conc. hydrochloric acid. The mixture was heated to 80° C. and vigorously stirred with 100 ml of an 80:20 mixture of xylene and tetrahydrofuran. The phases were separated and the aqueous phase was then extracted again with 50 ml of solvent mixture. Some of the solvent mixture was distilled off in vacuo to remove water from the dark-brown organic phase. About 80 ml of xylene remained in the distillation bottom. The distillation bottom was filtered hot and then slowly cooled to room temperature, the hydroxycarboxylic acid crystallizing. After a standing time of 16 hours, the crystallizate was filtered off and washed once with 25 ml of xylene and twice with 16 ml of xylene. After sucking dry, the solvent residues were removed at 60° C. and 10 mbar. 8.4 g of highly pure R-2-chloromandelic acid of 99.9%ee were obtained.

What is claimed is:

1. A process for the preparation of chemically and optically highly pure (R)- and (S)-α-hydroxycarboxylic acids, which comprises treating the hydrolysis solution obtained by acidic hydrolysis of the(R)- and (S)-cyanohydrins, prepared by enzyme-catalyzed addition of a cyanide group donor to the corresponding aldehydes or ketones, directly with an aromatic hydrocarbon, optionally in combination with a cosolvent selected from the group consisting of ethers and ketones, then extracting the mixture at hydrolysis temperature, whereupon after cooling of the organic phase the corresponding chemically and optically highly pure (R)- and (S)-α-hydroxycarboxylic acids having an optical purity of over 98%ee crystallize out.

2. The process as claimed in claim 1, wherein chemically and optically highly pure aromatic (R)- and (S)-α-hydroxycarboxylic acids of the formula Ar—$(CH_2)_n$CH(OH)$CO_2$H in which n is 0 or an integer from 1 to 5 and Ar is an aryl or heteroaryl radical which is unsubstituted or substituted by OH, $C_1$–$C_4$-alkyl or alkoxy, thioalkyl, halogen, optionally substituted phenyl or phenoxy, amino or nitro, are prepared.

3. The process as claimed in claim 1, wherein toluene, xylene, benzene, ethylbeazene, isopropylbenzene or chlorobenzenes are employed as aromatic hydrocarbons.

4. The process as claimed in claim 1, wherein the cosolvent employed is a solvent which increases the solubility of the hydroxycarboxylic acid in the organic phase and which is separable by distillation, in an amount from 5 to 50% by volume.

5. The process as claimed in claim 1, wherein the ether is tetrahydrofuran, methyl tert-butyl ether or dimethoxyethane.

6. The process according to claim 1, wherein the ketone is methylisobutyl ketone.

* * * * *